United States Patent
Oshlack et al.

(10) Patent No.: US 10,039,720 B2
(45) Date of Patent: Aug. 7, 2018

(54) TAMPER RESISTANT DOSAGE FORM COMPRISING CO-EXTRUDED, ADVERSE AGENT PARTICLES AND PROCESS OF MAKING SAME

(71) Applicant: Purdue Pharma L.P., Stamford, CT (US)

(72) Inventors: Benjamin Oshlack, Boca Raton, FL (US); Hua-Pin Huang, Englewood Cliffs, NJ (US)

(73) Assignee: PURDUE PHARMA L.P., Stamford, CT (US)

( * ) Notice: Subject to any disclaimer, the term of this patent is extended or adjusted under 35 U.S.C. 154(b) by 0 days.

(21) Appl. No.: 15/419,486

(22) Filed: Jan. 30, 2017

(65) Prior Publication Data

US 2017/0135959 A1 May 18, 2017

Related U.S. Application Data

(62) Division of application No. 10/554,157, filed as application No. PCT/US2004/012776 on Apr. 21, 2004, now Pat. No. 9,579,286.

(60) Provisional application No. 60/464,295, filed on Apr. 21, 2003.

(51) Int. Cl.
| | |
|---|---|
| *A61K 9/50* | (2006.01) |
| *A61K 31/485* | (2006.01) |
| *A61K 9/00* | (2006.01) |
| *A61K 9/48* | (2006.01) |

(52) U.S. Cl.
CPC .......... *A61K 9/5084* (2013.01); *A61K 9/0053* (2013.01); *A61K 9/4808* (2013.01); *A61K 9/5026* (2013.01); *A61K 9/5089* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 3,493,657 A | 2/1970 | Lewenstein et al. | |
| 3,773,955 A | 11/1973 | Pachter et al. | |
| 3,966,940 A | 6/1976 | Pachter et al. | |
| 4,457,933 A | 7/1984 | Gordon et al. | |
| 4,582,835 A | 4/1986 | Lewis et al. | |
| 4,880,585 A | 11/1989 | Klimesch et al. | |
| 4,957,681 A | 9/1990 | Klimesch et al. | |
| 4,970,075 A | 11/1990 | Oshlack | |
| 4,990,341 A | 2/1991 | Goldie et al. | |
| 5,073,379 A | 12/1991 | Klimesch et al. | |
| 5,266,331 A | 11/1993 | Oshlack et al. | |
| 5,324,351 A | 6/1994 | Oshlack et al. | |
| 5,334,392 A | 8/1994 | Cuine et al. | |
| 5,356,467 A | 10/1994 | Oshlack et al. | |
| 5,451,409 A | 9/1995 | Rencher et al. | |
| 5,462,747 A | 10/1995 | Radebaugh et al. | |
| 5,472,712 A | 12/1995 | Oshlack et al. | |
| 5,478,577 A | 12/1995 | Sackler et al. | |
| 5,492,692 A | 2/1996 | Digenis et al. | |
| 5,508,042 A | 4/1996 | Oshlack et al. | |
| 5,549,912 A | 8/1996 | Oshlack et al. | |
| 5,656,295 A | 8/1997 | Oshlack et al. | |
| 5,935,975 A | 8/1999 | Rose et al. | |
| 5,958,452 A | 9/1999 | Oshlack et al. | |
| 5,965,161 A | 10/1999 | Oshlack et al. | |
| 5,968,551 A | 10/1999 | Oshlack et al. | |
| 6,063,405 A | 5/2000 | Drizen et al. | |
| 6,120,802 A | 9/2000 | Breitenbach et al. | |
| 6,143,328 A | 11/2000 | Heafield et al. | |
| 6,194,000 B1 | 2/2001 | Smith et al. | |
| 6,228,863 B1 | 5/2001 | Palermo et al. | |
| 6,261,599 B1 | 7/2001 | Oshlack et al. | |
| 6,294,195 B1 | 9/2001 | Oshlack et al. | |
| 6,306,391 B1 | 10/2001 | Modi et al. | |
| 6,335,033 B2 | 1/2002 | Oshlack et al. | |
| 6,696,088 B2 * | 2/2004 | Oshlack | A61K 9/0043 424/400 |

(Continued)

FOREIGN PATENT DOCUMENTS

| | | |
|---|---|---|
| EP | 1064935 | 1/2001 |
| JP | 10-251149 | 9/1998 |

(Continued)

OTHER PUBLICATIONS

Supplemental European Search Report for EP 04 76 0176 dated Nov. 9, 2010, 3 pgs.
International Search Report for PCT/US04/12776 dated Jan. 4, 2005, 3 pgs.
Remington's Pharmaceutical Sciences, 16th ed. (A. Osol, ed.), Mack Publishing Co. Easton, PA, 1553-1593 (1980).
Remington's Pharmaceutical Sciences, 16th ed. (A. Gennaro, ed.), Mack Publishing Co. Easton, PA, 1684-1685 (1990).

(Continued)

*Primary Examiner* — Susan T Tran
*Assistant Examiner* — William Craigo
(74) *Attorney, Agent, or Firm* — Lowenstein Sandler LLP

(57) ABSTRACT

The present invention relates to co-extruded pharmaceutical compositions and dosage forms comprising an adverse agent, such as an opioid antagonist, which can be sequestered. The pharmaceutical compositions and dosage forms diversion of a dosage form containing an active pharmaceutical agent, such as an opioid. The present invention also relates to methods of treating a patient with such a dosage form, as well as kits containing such a dosage form with instructions for using the dosage form to treat a patient. The present invention further relates to a process for the preparation of such pharmaceutical compositions and dosage forms comprising co-extrusion of a core comprising an adverse agent and a sheath.

8 Claims, 1 Drawing Sheet

(56) References Cited

U.S. PATENT DOCUMENTS

| | | |
|---|---|---|
| 7,022,344 B1 | 4/2006 | Kothrade et al. |
| 7,144,587 B2 | 12/2006 | Oshlack et al. |
| 2002/0119197 A1* | 8/2002 | Dyar .................... A61K 9/0092 424/473 |
| 2003/0004177 A1 | 1/2003 | Kao et al. |
| 2003/0073714 A1 | 4/2003 | Breder et al. |
| 2003/0143269 A1 | 7/2003 | Oshlack et al. |
| 2003/0157168 A1 | 8/2003 | Breder et al. |
| 2003/0190362 A1 | 10/2003 | Sackler et al. |

FOREIGN PATENT DOCUMENTS

| | | |
|---|---|---|
| WO | 0158451 | 8/2001 |
| WO | WO 0158451 A1 * | 8/2001 ........... A61K 9/0043 |
| WO | 03/013433 | 2/2003 |
| WO | 03/013525 | 2/2003 |
| WO | 2004/026283 | 4/2004 |
| WO | 2004/093819 | 11/2004 |
| WO | 2005/055981 | 6/2005 |

OTHER PUBLICATIONS

Gandhi, et al., "Extrusion and spheronization in the development of oral controlled-release dosage forms," PSTT, Apr. 1999, pp. 160-170, vol. 2, No. 4.

\* cited by examiner

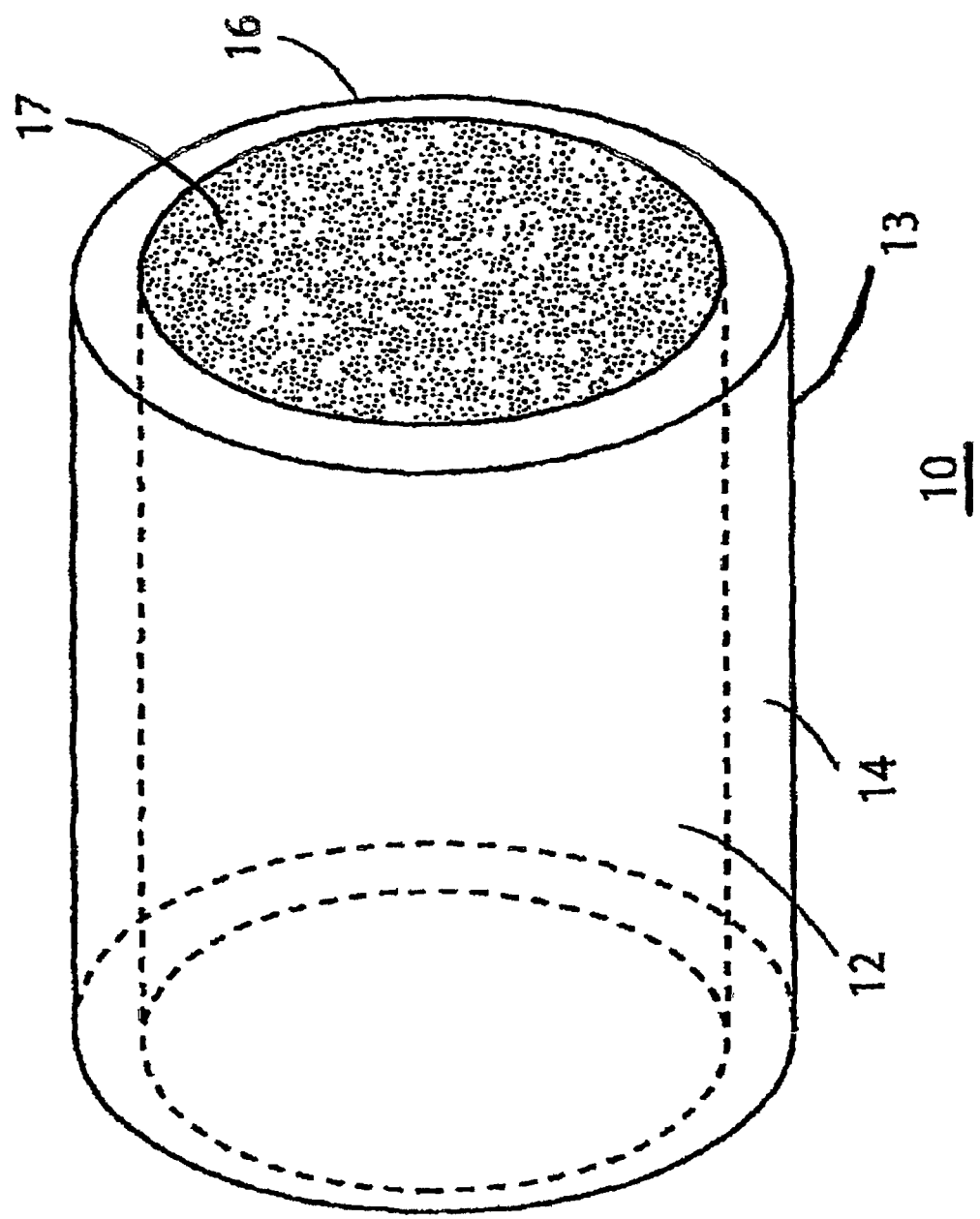

TAMPER RESISTANT DOSAGE FORM COMPRISING CO-EXTRUDED, ADVERSE AGENT PARTICLES AND PROCESS OF MAKING SAME

CROSS-REFERENCE TO RELATED APPLICATION(S)

This application is a divisional of U.S. patent application Ser. No. 10/554,157, filed on Sep. 13, 2006, which is a National Stage Entry of PCT/US04/12776 filed on Apr. 21, 2004, which claims the benefit of U.S. Provisional Application No. 60/464,295, filed Apr. 21, 2003. The contents of these applications are hereby incorporated by reference in their entirety.

1. FIELD OF THE INVENTION

The present invention relates to co-extruded pharmaceutical compositions and dosage forms comprising an adverse agent, such as an opioid antagonist, which can be sequestered. The pharmaceutical composition and dosage forms are useful for preventing or discouraging tampering, abuse, misuse or diversion of a dosage form containing an active pharmaceutical agent, such as an opioid. The present invention also relates to methods of treating a patient with such a dosage form, as well as kits containing such a dosage form with instructions for using the dosage form to treat a patient. The present invention further relates to a co-extrusion process for the preparation of such pharmaceutical compositions and dosage forms.

2. BACKGROUND OF THE INVENTION

Opioids, also known as opioid agonists, are a group of active pharmaceutical agents that exhibit opium- or morphine-like properties. More particularly, opioid agonists exhibit some form of opioid receptor activity. Opioids are employed primarily as moderate to strong analgesic agents.

There have been previous attempts in the art to increase the tamper resistance of opioid analgesic dosage forms. Prior approaches to developing tamper resistant dosage forms have included combining an opioid agonist with an opioid antagonist. Particular examples of such combinations include compositions comprising naloxone and morphine or oxymorphone (U.S. Pat. No. 3,493,657 to Lewenstein et al.); methadone and naloxone (U.S. Pat. No. 3,773,955 to Pachter et al.); methadol or acetyl methadol and naloxone (U.S. Pat. No. 3,966,940 to Pachter et al.); oxycodone and naloxone (U.S. Pat. No. 4,457,933 to Gordon et al.); and buprenorphine and naloxone (U.S. Pat. No. 4,582,835 to Lewis et al.).

U.S. Pat. No. 6,228,863 to Palermo et al. discloses an oral dosage form which combines an opioid agonist and an opioid antagonist such that at least two separation steps are required to isolate the agonist.

U.S. Pat. No. 5,935,975 to Rose et al. discloses a method for treating drug dependency by the combined administration of the drug, i.e. the agonist, and an antagonist of the drug.

PCT Publication No. WO 01/58451 entitled "Tamper Resistant Oral Opioid Agonist Formulations," is directed to decreasing the abuse potential associated with opioid analgesic dosage forms by the inclusion of a sequestered opioid antagonist in an opioid agonist dosage form.

In addition, it is known in the pharmaceutical art to prepare oral dosage forms which provide for controlled release of therapeutically active agents. Such controlled release compositions are used to delay absorption of at least a portion of the dose of the agent until it has reached certain portions of the gastrointestinal tract. Such controlled release of the agent serves to maintain a desired concentration of the agent in the blood stream for a longer duration than would occur if conventional immediate or rapid release dosage forms were to be administered.

Over the years, several different methods of preparing controlled release pharmaceutical dosage forms have been suggested, including, for example, extrusion, granulation, coating beads and the like.

There remains a need in the art for improved tamper resistant dosage forms and improved techniques for their preparation.

3. SUMMARY OF THE INVENTION

The present invention relates to co-extruded, pharmaceutical compositions and dosage forms comprising an adverse agent, which can be a sequestered adverse agent, and co-extrusion methods for making such compositions and dosage forms. The present invention also relates to methods of treating a patient with such pharmaceutical compositions or dosage forms, as well as kits comprising such pharmaceutical compositions or dosage forms and instructions directing the usage of the composition or dosage form to treat a patient.

In one embodiment, the invention relates to dosage forms comprising a plurality of co-extruded particles comprising an adverse agent, which can be a sequestered adverse agent. The adverse agent particles can comprise a core and a sheath which at least partially surrounds the core. The core can preferably comprise an adverse agent and at least one hydrophobic material and the sheath may preferably comprise at least one hydrophobic material. In one embodiment, the adverse agent is present only in the core. In another embodiment, the sheath is substantially devoid of an adverse agent. The dosage forms in accordance with the present invention include oral dosage forms, such as capsules or tablets, rectal suppositories and vaginal suppositories.

In another embodiment, the invention relates to dosage forms comprising a plurality of first particles comprising an active agent, and a plurality of second particles comprising an adverse agent, which can be a sequestered adverse agent. The second particles comprise a core comprising a sequestered adverse agent and a sheath.

In one embodiment, the invention also relates to dosage forms comprising a plurality of first particles comprising an opioid agonist, wherein the first particles provide controlled release of the opioid agonist upon administration to a patient; and a plurality of co-extruded second particles comprising a core comprising a sequestered adverse agent and a sheath.

In certain embodiments, the present invention also relates to methods of forming a plurality of sequestered adverse agent particles comprising forming a sheath comprising a hydrophobic material and a core comprising a sequestered adverse agent and a hydrophobic material, wherein the sheath at least partially surrounds the core.

In yet another embodiment, the invention relates to methods of making a dosage form comprising: (i) forming a plurality of first particles comprising an active agent; (ii) forming a plurality of second particles comprising an adverse agent by forming a core composition and a sheath composition to form a strand, wherein the sheath composition comprises a hydrophobic material and radially surrounds the core composition at least partially and the core composition comprises the adverse agent and a hydrophobic material and cutting the strand to form a plurality of second particles; and (iii) adding the first particles and the second particles together in a form suitable for administration to a patient.

The present invention further relates to methods of treating a patient, comprising administering a dosage form of the invention to the patient. In one embodiment of the invention, the patient is treated for pain.

The present invention also includes a method of reducing abuse, misuse or diversion of a dosage form for treating pain, comprising administering to a patent in need thereof a dosage form of the invention.

In still another embodiment, the invention relates to kit for treating pain in a patient, comprising at least one dosage form of the invention and a set of instructions describing the use of the dosage form to treat the patient. In one embodiment of the invention, the kit is for treating a patient's pain.

The present invention may be understood more fully by reference to the following detailed description and examples, which are intended to exemplify non-limiting embodiments of the invention.

4. BRIEF DESCRIPTION OF THE DRAWINGS

FIG. 1 is a perspective view of one embodiment of an adverse agent-containing particle of the present invention, which comprises a cylindrical particle (10) containing a sequestered adverse agent wherein a core (12) comprises an adverse agent and the core is radially surrounded by a sheath (14).

5. DETAILED DESCRIPTION OF THE INVENTION

5.1 Definitions

Any reference herein to any pharmaceutical agent, such as an active agent, an adverse agent, an opioid agonist or an opioid antagonist, shall, unless otherwise stated, include any pharmaceutically acceptable form of such pharmaceutical agent, such as the free form, any pharmaceutically acceptable salt form, any pharmaceutically acceptable base form, any pharmaceutically acceptable hydrate, any pharmaceutically acceptable solvate, any stereoisomer, any optical isomer, as well as any prodrug of such pharmaceutical agent and any pharmaceutically active analog of such pharmaceutical agent, and mixtures of any of the foregoing.

The phrase "pharmaceutically acceptable salt," as used herein, can be a salt formed from an acid and the basic group, such as a nitrogen group, of an active agent or an adverse agent. Generally, examples of such salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, glubionate and pamoate (i.e., 1,1'-methylene-bis-(2-hydroxy-3-naphthoate)) salts. The term "pharmaceutically acceptable salt" can alternatively be a salt prepared from an active agent or an adverse agent having an acidic functional group, such as a carboxylic acid or sulfonic acid functional group, and a pharmaceutically acceptable inorganic or organic base. Generally, examples of such bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methylamine, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

A "patient" or "animal" is preferably a mammal, and includes, but is not limited to, a cow, monkey, horse, sheep, pig, chicken, turkey, quail, cat, dog, mouse, rat, rabbit, and guinea pig, and most preferably a human.

As used herein, the phrase "active agent" refers to a pharmaceutical agent that causes a biological effect when absorbed into the blood stream of a patient.

As used herein, the phrase "adverse agent" refers to a pharmaceutical agent that partially or completely negates or reverses at least one biological effect of the active agent, e.g. euphoric effect, or produces one or more unpleasant physiological reactions, e.g., vomiting, nausea, diarrhea, bad taste, when absorbed in sufficient amount into the blood stream of a patient or animal.

As used herein, the term "controlled release" refers to the in vivo release of an active agent from a dosage form following administration at a rate which will provide a longer duration of action than a single dose of the normal (i.e., immediate release) dosage form. For example, a typical immediate release oral dosage form may release the drug, e.g., over a 1 hour interval, as compared to a controlled release oral dosage form which may release the drug, e.g., over a 4 to 24 hour interval.

As used herein, the phrase "opioid agonist" refers to an active agent which binds, optionally stereospecifically, to any one or more of several subspecies of opioid receptors and produces agonist activity.

As used herein, the phrase "opioid antagonist" refers to an adverse agent that either reduces at least one biological effect of an opioid agonist, e.g., euphoric effect, or elicits at least one unpleasant physiological reaction when absorbed in sufficient amount into the blood stream of a patient or animal.

As used herein, the phrase "sheath substantially devoid of an adverse agent" refers to a sheath that does not contain any adverse agent except for, possibly, small amounts which may have migrated into the sheath from an extruded or co-extruded component, e.g., the core.

5.2 Dosage Forms Comprising an Adverse Agent

In one embodiment, the adverse agent is not sequestered. In that embodiment, the adverse agent can be released in vivo at any rate, including but not limited to immediate release or controlled release.

As stated above, one embodiment of the present invention is directed to co-extruded pharmaceutical compositions and dosage forms comprising an adverse agent, which can be a sequestered adverse agent, and to methods of making such compositions and dosage forms.

In one embodiment, the invention relates to dosage forms comprising a plurality of co-extruded particles comprising a sequestered adverse agent. Those compositions and dosage forms of the invention are formulated or made in a manner which greatly reduces, limits or prevents the in vivo release or absorption of the sequestered adverse agent into the blood stream following administration as intended of the intact dosage form to a patient. Thus, only a small amount, preferably less than about 10% by weight and more preferably less than about 1% by weight or none, of the adverse agent present in the dosage form is released in vivo or absorbed into the blood stream following the administration as intended of an intact dosage form to a patient. When the adverse agent is an opioid antagonist, preferably less than about 0.5 mg, and more preferably less than about 0.05 mg, of the opioid antagonist is released in vivo following administration as intended of the intact dosage form to a patient.

The adverse agent can be sequestered by co-extruding: a) the adverse agent with a material which limits or delays the in vivo release of the adverse agent to form a core; and b) a sheath which at least partially covers or surrounds the core. In one embodiment, the adverse agent can be extruded with at least one hydrophobic material and, optionally, binders, plasticizers and/or excipients. In one embodiment, the sheath can comprise at least one hydrophobic material and, optionally, binders, plasticizers and/or excipients. The core is at least partially surrounded or covered by the sheath, and a portion of the adverse agent-containing core can be exposed. In one embodiment, the sheath covers or surrounds a majority of the core. For example, when the core is cylindrical, the sheath can radially surround the length of the core while leaving the ends of the core exposed in the axial direction.

In one embodiment, the present invention relates to solid dosage forms comprising a plurality of co-extruded particles comprising a sequestered adverse agent, wherein the particles comprise a core containing the adverse agent and the core is at least partially surrounded by a sheath. The particles are made by co-extrusion of the core and the sheath. Preferably, the sheath surrounds a majority, but not all, of the core component. In one embodiment, the co-extruded, sequestered adverse agent particle comprises an adverse agent-containing core and a sheath; the core comprising an adverse agent and a hydrophobic matrix material; and the sheath comprising a hydrophobic matrix material; wherein the core is at least partially surrounded by a sheath.

In one embodiment, the invention relates to dosage forms comprising: (i) a plurality of first particles comprising an active agent; and (ii) a plurality of co-extruded second particles comprising a core comprising a sequestered adverse agent and a sheath, as well as methods of their preparation and use. In one embodiment, co-extruded particles containing a sequestered adverse agent ("sequestered adverse agent particles") can be combined with particles comprising an active agent to form a dosage form for administration to a patient. For example, a plurality of co-extruded, sequestered adverse agent particles and a plurality of particles containing an active agent ("active agent particles") can be placed together in a capsule or compressed together to form a tablet, caplet, suppository or other dosage form.

The dosage forms of the invention can be administered orally, such as in the form of a tablet or capsule, or rectally or vaginally in the form of a suppository. In a preferred embodiment, the invention is directed to oral dosage forms.

In one embodiment, the sequestered adverse agent can be incorporated into small particles, such as, for example, particles having a size of from about 0.1 mm to about 3.0 mm in all dimensions. The particles can have any shape, such as cylindrical, spherical, square or irregular.

In certain embodiments, the adverse agent can be present throughout the co-extruded, sequestered adverse agent particle. In one embodiment, the adverse agent can be present in only the core, or in both the core and the sheath. In another embodiment, the adverse agent can be present in one or more inner layers of a co-extruded, multilayer particle.

Multiparticulate extrudates of the invention can be compressed into an oral tablet using conventional tableting equipment and standard techniques. Techniques and compositions for making tablets (compressed and molded), capsules (hard and soft gelatin) and other forms of pills are also described in Remington's Pharmaceutical Sciences (Arthur Osol, editor), 1553-1593 (1980), incorporated by reference herein.

In one embodiment, an oral dosage form is prepared to include an effective amount of melt-extruded multiparticulates ("MEMs") within a hard or soft gelatin capsule. For example, a plurality of co-extruded MEMs containing an adverse agent and a plurality of MEMs containing an active agent can be placed in a gelatin capsule in an amount sufficient to provide an effective sustained-release dose of the active agent when ingested and contacted by body fluid, without significant release of the sequestered adverse agent. Alternatively, only the adverse agent can be formulated in MEMs.

In another embodiment, the MEMs can be compressed into tablets as set forth in U.S. Pat. No. 4,957,681 (Klimesch, et al.), which is expressly incorporated herein by reference.

In certain embodiments, in the co-extruded, adverse agent containing particles, the adverse agent is present only in a core ("adverse agent core") of a particle having a core and a sheath. The adverse agent core is surrounded at least partially by a sheath. Both the core and the sheath preferably comprise at least one hydrophobic material which acts as a retarding agent to limit the in vivo dissolution of the particle after administration. The hydrophobic material of the core may or may not be the same as the hydrophobic material of the sheath. The particle size of the adverse agent-containing particle is preferably from about 0.1 mm to about 5.0 mm in all dimensions and, more preferably, from about 0.1 mm to about 3.0 mm in all dimensions. In one preferred embodiment, the adverse agent is sequestered within the core of a cylindrical particle, and the core is radially surrounded by the sheath, leaving the core exposed at one or both ends of the co-extruded, cylindrical particle. Such particle can be manufactured by co-extrusion of the core and the sheath, followed by rendering the co-extruded strand into particles, as discussed in further detail below.

In certain embodiments, the present invention includes a dosage form which includes a plurality of first particles containing an active agent and a plurality of co-extruded second particles containing a sequestered adverse agent. In certain embodiments, the active agent particles are formulated to provide controlled release of the active agent in vivo over at least 8 hours, preferably over at least 12 hours, more preferably over at least 24 hours, or longer. The active agent particles can be made according to any method known in the art, such as by extrusion, melt-extrusion, granulation, coating inert beads, etc.

In certain embodiments, the active agent particles and the co-extruded, sequestered adverse agent particles are similar, and preferably, identical in size and appearance, to reduce the likelihood that they could be manually separated from each other.

The co-extruded, sequestered adverse agent particles are formulated so that only a relatively small amount, and preferably none, of the sequestered adverse agent is released in vivo when the co-extruded, sequestered adverse agent particles are administered intact to a patient, as intended.

When an intact dosage form including active agent particles and co-extruded, sequestered adverse agent particles is administered to a patient, only a relatively small amount, and preferably almost none, of the sequestered adverse agent is released in vivo, whereas the active agent is released at the intended rate, which can vary from immediate release to controlled release. However, when a dosage form comprising active agent particles and co-extruded, sequestered adverse agent particles is tampered with, e.g., chewed, crushed, ground or dissolved, particularly in a solvent with heat (e.g., greater than from about 45° C. to about 50° C., up to about 100° C. or above), then the amount of adverse agent available for absorption into the body is substantially increased. The adverse agent is then available to exert its effect by either reducing at least one effect of the active agent, e.g., euphoric effect, or eliciting one or more unpleasant effects in the patient. Thus, where the adverse agent is an antagonist of the active agent, at least one effect of the active agent is preferably substantially diminished, or even eliminated, by the effect of the adverse agent. For example, where the active agent is an opioid agonist and the adverse agent is an opioid antagonist, a greatly increased amount of opioid antagonist will become bioavailable when the dosage form is tampered with, interfering with opioid-receptor binding and reducing the opioid agonist's euphoric effect. Accordingly, only patients who take the dosage form of the present invention as intended, i.e., as an intact dosage form, will experience substantially the full pharmacological effect of the therapeutic agent. Where the adverse agent is an emetic agent and the dosage form is tampered with, the immediate release and absorption of the emetic agent will induce nausea and/or vomiting to discourage the user from tampering with the dosage form and also to remove the therapeutic agent from the subject's body. Abuse of the active agent in the dosage form will thus become less desirable because of the undesirable effects caused by the adverse agent.

When administered intact to a patient, the in vivo release of any adverse agent from the dosage form will preferably be sufficiently low so that it will not substantially reduce the benefits of the active agent or produce any unpleasant physiological reaction. The release rate of the adverse agent will be determined in large part by the composition of the adverse agent core and the sheath of the co-extruded, sequestered adverse agent particle. The co-extruded, sequestered adverse agent particle will preferably release less than about 10% by weight and, more preferably, less than about 1% by weight or none, of the adverse agent in vivo following administration of the intact dosage form. When the adverse agent is an opioid antagonist, the sequestered adverse agent particles, in total, will preferably release less than about 0.5 mg, more preferably less than about 0.05 mg, of the opioid antagonist in vivo following administration of the intact dosage form. For example, when the oral dosage form contains 5.0 mg of sequestered opioid antagonist and a dissolution test is conducted using the USP Basket Method (USP Type I basket, 100 rpm; 700 ml simulated gastric filled, pH 1.2 without enzyme; 37° C. for 1 hour followed by 900 ml simulated intestinal fluid; pH 7.5 without enzyme for the duration of the test), the quantity of opioid antagonist released in a simulated gastrointestinal fluid over 36 hours is less than 0.5 mg, and more preferably less than 0.05 mg.

In one embodiment of the invention, the active agent particles and the co-extruded, sequestered adverse agent particles are approximately, and preferably exactly, the same color, size and shape so as to make it difficult to distinguish the two types of particles from each other. Both types of particles can be covered by a cosmetic coating so as to render them similar in appearance. Any known type of cosmetic coating used for pharmaceutical oral dosage forms can be used so long as the dissolution pattern of the two particle types achieve the intended purpose of the invention.

In certain embodiments, either the dosage form or the active agent particles and/or the co-extruded, sequestered adverse agent particles can be cured by exposure to prolonged elevated temperatures in order to achieve increased stability. As used herein, the term "curing" means the heat treatment of the dosage form (or intermediate product) for purposes of obtaining a stabilized final dosage form. As will be understood by those skilled in the art, when the formulations of the invention incorporate a polymer as part or all of the hydrophobic retarding agent, a heat treatment causes a curing effect and the polymer possibly cross-links with itself into a more stable state. When the formulations of the invention include a hydrophobic material such as, e.g., hydrogenated vegetable oil or stearyl alcohol, the heat treatment may be more akin to annealing of the formulation rather than a curing of the polymer. However, for purposes of the present invention, the use of the term "curing" is deemed to encompass both curing and annealing. In situations where the hydrophobic material includes only a wax-like substance, curing can be accomplished at a temperature from about 35° C. to about 65° C., for a time period sufficient to achieve maximum stability, such as for a time period from about 4 to about 72 hours. In other embodiments, curing is conducted at a temperature of from about 40° C. to about 60° C., for a time period from about 5 to about 48 hours or more, and preferably at least about 24 hours. Suitable curing times that achieve the intended result of a stabilized dosage form can be determined by those of skill in the art.

5.3 Adverse Agent

As noted above, the present invention is directed to co-extruded dosage forms and pharmaceutical compositions comprising a sequestered adverse agent, as well as methods for making and administering such dosage forms and compositions. In one embodiment, the invention relates to dosage forms comprising a plurality of co-extruded particles comprising a sequestered adverse agent.

The sequestered adverse agent can be any pharmaceutical active agent which at least partially reduces or blocks the biological effect of an active agent or which creates an unpleasant effect when absorbed into an animal's or a patient's blood stream. Examples of adverse agents include, but are not limited to, antagonists of any therapeutically active agonist. When an opioid agonist is used as the active agent in the dosage form of the present invention, an opioid antagonist can be used as the adverse agent. Likewise, when a benzodiazepine is used as the active agent in the dosage form of the present invention, a benzodiazepine antagonist can be used as the adverse agent. When a barbiturate is used as an active agent in the dosage form of the present invention, a barbiturate antagonist can be used as the adverse agent. When an amphetamine is used as an active agent in the dosage form of the present invention, an amphetamine antagonist can be used as the adverse agent. When the active agent is toxic when dosed above its normal therapeutic range, i.e., when there is a significant potential for an overdose, then an antidote of the toxic active agent can be used as the adverse agent.

In one embodiment, the adverse agent is an opioid antagonist. Opioid antagonists useful in the present invention include, but are not limited to, naloxone, naltrexone, nalmefene, nalbuphine, nalorphine, cyclazacine, cyclazocine, levallorphan, pharmaceutically acceptable salts thereof, and mixtures thereof.

Useful opioid antagonist salts include salts formed from an acid and the basic nitrogen group of an opioid antagonist. Examples of opioid antagonist salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Other opioid antagonist salts include salts prepared from an antagonist having an acidic functional group, such as a carboxylic acid or sulfonic acid functional group, and a pharmaceutically acceptable inorganic or organic base. Suitable bases include, but are not limited to those identified above in Section 5.1 in the paragraph which references the term "pharmaceutically acceptable salt".

In certain embodiments, the opioid antagonist is nalmefene, naloxone, naltrexone, or a pharmaceutically acceptable salt thereof. In another embodiment, the opioid antagonist is a naltrexone salt, such as naltrexone hydrochloride.

Benzodiazepine antagonists that can be used as the adverse agent of the present invention include, but are not limited to, flumazenil.

Barbiturate antagonists which can be used as the adverse agent of the present invention include, but are not limited to, amphetamines, as described herein.

Stimulant antagonists that can be used as the adverse agent of the present invention include, but are not limited to, benzodiazepines, described herein.

In another embodiment of the present invention, the adverse agent is an agent that causes an undesired physiological reaction, such as emesis. This type of adverse agent can be used with any kind of therapeutic agent including an opioid, a benzodiazepine, a barbiturate, or a stimulant. Examples of emetic agents suitable for use as the adverse agent in the present invention includes any drug that safely and effectively induces vomiting after administration including, but not limited to, ipecac and apomorphine.

5.4 Active Agent

The active agent of the present invention may or may not be formulated in a plurality of particles.

Any kind of active agent can be used in the dosage forms of the present invention. Examples of useful active agents include, but are not limited to, analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile-dysfunction-improvement agents, immunosuppressants, anti-protozoal agents, anti-thyroid agents, anxiolytic agents, sedatives, hypnotics, neuroleptics, β-blockers, cardiac ionotropic agents, corticosteroids, diuretics, anti-parkinsonian agents, gastrointestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, and non-essential fatty acids. The active agent particles can comprise more than one active agent.

More specific examples of active agents include, but are not limited to, opioids, benzodiazepines, barbiturates, and stimulants, such as methylphenidate and amphetamines, dronabinol, glutethimide, methylphenidate, nabilone, anabolic steroids, methylprylon, ethchlorovynol, ethinamate, fenfluramine, meprobamate, pemoline, levomethadyl, benzphetamine, chlorphentermine, diethylpropion, phentermine, mebutamate, chlortermine, phenylacetone, dronabinol, nabilone, benphetamine, chloral hydrate, ethclorovynol, paraldehyde, midazolam, and detropropoxyphene.

In certain embodiments, the active agent is an opioid agonist. Useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, pharmaceutically acceptable salts thereof, and mixtures thereof.

In certain embodiments, the opioid agonist is selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol and mixtures thereof. In one embodiment, the opioid agonist is oxycodone, hydromorphone or hydrocodone.

The term "benzodiazepines" refers to benzodiazepine and drugs that are derivatives of benzodiazepine and are able to depress the central nervous system. Benzodiazepines include, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate and mixtures thereof.

Barbiturates refer to sedative-hypnotic drugs derived from barbituric acid (2,4,6,-trioxohexahydropyrimidine) Barbiturates include, but are not limited to, amobarbital, aprobarbotal, butabarbital, butalbital, methohexital, mephobarbital, metharbital, pentobarbital, phenobarbital, secobarbital and mixtures thereof.

Stimulants refer to drugs that stimulate the central nervous system. Stimulants include, but are not limited to, amphetamines, such as amphetamine, dextroamphetamine resin complex, dextroamphetamine, methamphetamine, methylphenidate and mixtures thereof.

The active agent can be an agent intended for delivery to the colon, including, but not limited to, agents that act locally in the colonic region to treat a colon diseases such as irritable bowel syndrome, irritable bowel disease, Crohns disease, constipation, post operative atony, gastrointestinal infections, and therapeutic agents that deliver antigenic material to the lymphoid tissue. Active agents for the treatment of colon disease include, but are not limited to 5-ASA; steroids, such as hydrocortisone and budesonide; laxatives; stool softeners; octreotide; cisapride; anticholinergics; opioids; calcium channel blockers; DNA for delivery to the cells of the colon; glucosamine; thromboxane $A_2$ synthetase inhibitors, such as Ridogrel; 5HT3-antagonists, such as ondansetron; antibodies against infectious bacteria, such as *Clostridium difficile*; and antiviral agents, for example, for the prophylaxis of HIV.

Alternatively, the active agent can be an agent that is systemically active and for which absorption is improved in the colon region. Such drugs include polar compounds such as: heparins; insulin; calcitonins; human growth hormone (HGH); growth hormone releasing hormone (GHRH); interferons; somatostatin and analogues such as octreotide and vapreotide; erythropoietin (EPO); granulocyte colony stimulating factor (GCSF); parathyroid hormone (PTH); luteinising hormone releasing hormone (LHRH) and analogues thereof; atrial natriuretic factor (ANF); vasopressin; desmopressin; calcitonin gene related peptide (CGRP); and analgesics.

The active agent particles can further comprise hydrophobic materials, binders, plasticizers, excipients, and combinations thereof. Suitable matrix materials include those which allow release of the active agent at a rate sufficient to achieve the desired result, e.g., immediate release or sustained release. In one embodiment, permeable matrix material is used, allowing for diffusive release of the opioid agonist into the gastrointestinal fluid.

5.5 Adverse Agent Particles

In accordance with the present invention, the adverse agent is formulated in a co-extruded multilayer particle. In certain preferred embodiments, the adverse agent is sequestered in a co-extruded, two layer particle comprising a sheath which at least partially surrounds the core, and, preferably surrounds a majority of the core. For example, FIG. 1 is a perspective view of one non-limiting embodiment of the present invention comprising a co-extruded, cylindrical particle (10). The sequestered adverse agent is contained within a core (12). The majority of the core is surrounded by a sheath (14). For example, the core can be cylindrical with the sheath covering the outer curved surface (13) of the core in the radial direction, leaving at least one end (17) of the core uncovered in the axial direction. In FIG. 1, an uncovered area of the core at one end of the cylindrical particle (16) is depicted by the shaded area (17).

5.5.1 Core

The sequestered adverse agent-containing core of the present invention preferably comprises a hydrophobic matrix material. Hydrophobic matrix materials useful in the present invention include those that are known in the art to be insoluble or to have a low solubility in the gastrointestinal tract. Such materials include, but are not limited to, a hydrophobic material selected from the group consisting of acrylic and methacrylic acid polymers and copolymers, and alkylcelluloses. The matrix can also include additional hydrophobic materials such as zein, shellac, hydrogenated castor oil, hydrogenated vegetable oil or mixtures thereof. Although insoluble, such hydrophobic materials can degrade over time, thereby eventually releasing some portion of the adverse agent. One of ordinary skill in the pharmaceutical arts can control the rate of such release by, for example, altering the content of the hydrophobic matrix material in the adverse agent core in order to limit or greatly limit the in vivo release of the sequestered adverse agent. This and other methods of sequestering the adverse agent will be known in the art or can be determined by routine experimentation.

In one embodiment, the hydrophobic matrix material comprises acrylic polymers. Examples of suitable acrylic polymers include, but are not limited to acrylic acid and methacrylic acid copolymers, methyl methacrylate copolymers, ethoxyethyl methacrylates, cyanoethyl methacrylates, aminoalkyl methacrylate copolymer, poly(acrylic acid), poly(methacrylic acid), methacrylic acid alkylamide copolymers, poly(methyl methacrylate), polymethacrylate, poly (methyl methacrylate) copolymer, poly(methacrylic acid) (anhydride), methyl methacrylate, polyacrylamide, aminoalkyl methacrylate copolymer, poly(methacrylic acid anhydride), and glycidyl methacrylate copolymers. Additional examples of suitable acrylic polymers include, but are not limited to, acrylic resins comprising copolymers synthesized from acrylic and methacrylic acid esters (e.g., the copolymer of acrylic acid lower alkyl ester and methacrylic acid lower alkyl ester) containing about 0.02 to 0.03 moles of a tri (lower alkyl) ammonium group per mole of acrylic and methacrylic monomer.

The acrylic polymer can comprise one or more ammonio methacrylate copolymers. Ammonio methacrylate copolymers are well known in the art, and are fully polymerized copolymers of acrylic and methacrylic acid esters with a low content of quaternary ammonium groups. In order to obtain a desirable dissolution profile for a given therapeutic agent, it might be necessary to incorporate two or more ammonio methacrylate copolymers having differing physical properties. For example, it is known that by changing the molar ratio of the quaternary ammonium groups to neutral (meth) acrylic esters, the permeability properties of the resultant coating can be modified. One of ordinary skill in the art will readily be able to combine monomers to provide a copolymer that releases the therapeutic agent at the desired release rate. Copolymers of acrylate and methacrylate having a quaternary ammonium group functionality are commercially available as EUDRAGIT RS™ and EUDRAGIT RL™ (Röhm Pharma, GmbH, Darmstadt, Germany). Preferred ammonio methacrylate resins include EUDRAGIT RS™ in all forms, such as EUDRAGIT RS PO™. EUDRAGIT RS™ is known to be a water-insoluble copolymer of ethyl acrylate (EA), methyl methacrylate (MM) and trimethylammonium ethyl methacrylate chloride (TAM) in which the molar ratio of EA:MM:TAM is 1:2:0.01; see, e.g., U.S. Pat. No. 6,306,391. EUDRAGIT RS PO™ is known to be a powdered form of EUDRAGIT RS™; see, e.g., U.S. Pat. No. 5,492,692.

In one embodiment the hydrophobic matrix material comprises a water insoluble cellulose polymer. In certain embodiments, the cellulose polymer is a cellulose ether, a cellulose ester, or a cellulose ester ether. Preferably, the cellulose polymers have a degree of substitution ("D.S.") on the anhydroglucose unit of from about zero up to and including about 3. As used herein the term D.S. means the average number of hydroxyl groups present on the anhydroglucose unit of the cellulose polymer that are replaced by a substituent group. Representative cellulose polymers include, but are not limited to, polymers selected from cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and mono-, di-, and tricellulose alkenylates. Exemplary cellulose polymers include cellulose acetate having a D.S. of from about 1 to about 2 and cellulose acetate having a D.S. of from about 2 to about 3. Preferably, the cellulose polymer is ethylcellulose, cellulose acetate, cellulose propionate (low, medium, or high molecular weight), cellulose acetate propionate, cellulose acetate butyrate, cellulose acetate phthalate, or cellulose triacetate. A more preferred cellulose is ethylcellulose.

More specific cellulose polymers include cellulose propionate having a D.S. of about 1.8; cellulose acetate butyrate having a D.S. of about 1.8; cellulose triacylate having a D.S. of about 2.9 to 3, such as cellulose triacetate, cellulose trivalerate, cellulose trilaurate, cellulose tripalmitate, cellulose trisuccinate, and cellulose trioctanoate; cellulose diacylates having a D.S. of about 2.2 to 2.6 such as cellulose disuccinate, cellulose dipalmitate, cellulose dioctanoate, cellulose dipentanoate; and coesters of cellulose such as cellulose acetate butyrate, cellulose acetate octanoate butyrate, and cellulose acetate propionate.

The core can generally comprise from about 30% to about 99% by weight of one or more hydrophobic matrix materials, preferably from about 50% to about 95% by weight of the one or more hydrophobic matrix materials, more preferably from about 60% to about 95% by weight of the one or more hydrophobic matrix materials.

The adverse agent-containing core can optionally comprise one or more binders, additional retardants, plasticizers, and/or excipients. Binders are useful for maintaining the integrity of the matrix and may also help to delay the release of an agent into the bodily fluid. Examples of binders include natural and synthetic waxes, water insoluble waxes, fatty alcohols, fatty acids, hydrogenated fats, fatty acid esters, fatty acid glyercides, hydrocarbons, and hydrophobic and hydrophilic polymers having hydrocarbon backbones, and mixtures such as, stearyl alcohol, stearic acid, and water soluble polymers such as hydroxycelluloses.

Plasticizers are useful when the hydrophobic matrix material contains cellulose polymer or an acrylic polymer. Non-limiting examples of suitable plasticizers include, e.g., acetyl triethyl citrate and/or acetyl tributyl citrate.

The adverse agent core can also include other excipients, which may be added to improve the processability of the formulation during extrusion and/or to improve the properties of the final product. Non-limiting examples of liquid excipients include water and oils, including those of petroleum, animal, vegetable, or synthetic origin, such as peanut oil, soybean oil, mineral oil, sesame oil, castor oil, triglycerides and the like. Examples of solid excipients include magnesium stearate, saline, gum acacia, gelatin, starch paste, talc, keratin, colloidal silica, urea and the like. Coloring agents may also be added to the core.

5.5.2 Sheath

The co-extruded, sequestered adverse agent-containing particle of the present invention comprises a sheath which at least partially surrounds the adverse agent-containing core, and preferably surrounds a majority of the adverse agent-containing core. In one preferred embodiment, the sheath surrounds a majority, but not all, of the core. The sheath preferably comprises a hydrophobic matrix material and, optionally, binders, additional retardants, plasticizers and excipients. While the sheath can contain a small percentage of adverse agent, it is preferred that the sheath does not contain any adverse agent.

In one embodiment, the hydrophobic material of the sheath comprises one or more materials selected from the group consisting of acrylic and methacrylic acid polymers and copolymers, and water insoluble alkylcelluloses as described above for the core. The sheath can optionally comprise one or more additional hydrophobic materials, such as shellac, zein, hydrogenated castor oil, hydrogenated vegetable oil and mixtures thereof as described above for the core.

The hydrophobic matrix material used in the sheath may or may not be the same as that used in the adverse agent-containing core. Although the hydrophobic material used in the sheath will preferably be substantially insoluble in the gastrointestinal tract, this material could dissolve or biodegrade in vivo to some limited extent over time, thereby permitting the in vivo release from the core of a small amount of the adverse agent. One of ordinary skill in the pharmaceutical arts can control and limit the rate of such release, for example, by altering the composition of the sheath, increasing the thickness of the sheath, surrounding a larger portion of the core with the sheath, varying the size and/or dimensions of the core and/or varying the composition of the sheath and/or core. These and other methods will be known to one of ordinary skill in the art or can be determined by routine experimentation in view of this disclosure.

The sheath can comprise from about 10% to about 99% by weight, preferably from about 40% to about 95% by weight, and more preferably from about 60% to about 90% by weight of the one or more hydrophobic matrix materials.

The sheath can further comprise one or more additional retardants or one or more binders or plasticizers or excipients, or some combination thereof, such as those described above for the adverse agent-containing core.

5.6 Active Agent Particles

The present invention includes compositions and dosage forms comprising an active agent which can be formulated into any suitable dosage form, including but not limited to, active agent containing particles. The compositions and dosage forms of the invention can provide any rate of release of the active agent in vivo following oral administration, such as immediate release or controlled release. In preferred embodiments, active agent-containing particles provide a controlled release of the active agent, such as an opioid agonist. Formulations and methods of manufacture of controlled release dosage forms of opioid antagonists are known in the art. For example, U.S. Pat. Nos. 5,958,452; 5,965,161; 5,968,551; 6,294,195 and 6,335,033, each of which is expressly incorporated herein by reference, disclose controlled release oral opioid agonist dosage forms. The disclosure of one or more of such patents includes details such as formulations, matrix materials, coating materials, hydrophobic materials, retardants, binders, plasticizers, and excipients, as well as methods of coating beads, methods of forming spheroids, granulation methods (wet and dry), and extrusion methods for forming tablets, caplets and multiparticulate capsules for controlled release oral opioid agonist dosage forms.

The active agent can be dispersed in a matrix which provides controlled release of the active agent in vivo following oral administration. Any controlled-release matrix can be used to make active agent particles. Certain controlled-release matrices are known for oral formulations (see, e.g., Remingtons Pharmaceutical Sciences, 18$^{th}$ ed. Mack Publishing Co., Easton, Pa., 1990, p. 1684-1685). In addition to the controlled release matrices disclosed in the above-identified patents, other examples of useful controlled-release matrices are described in U.S. Pat. Nos. 6,143,328; 6,063,405; 5,462,747; 5,451,409; 5,334,392; 5,266,331, 5,549,912, 5,508,042, 5,656,295, 5,324,351, 5,356,467, and 5,472,712, the contents of which are expressly incorporated herein by reference.

The controlled-release matrix can include fusible hydrophobic material(s), optionally combined with hydrophilic material(s). The hydrophobic fusible material(s) can be, for example, a hydrophobic polymer or a natural or synthetic wax or oil, such as hydrogenated vegetable oil or hydrogenated castor oil, which can, for example, have a melting point of from about 45° C. to about 100° C., and in one embodiment from about 50° C. to about 90° C. The hydrophilic material can be a hydrophilic polymer such as a hydroxycellulose; a water soluble fusible material, such as polyethylene glycol; or a water soluble particulate material, such as dicalcium phosphate or lactose.

While any known method can be used to make controlled release opioid agonist particles for use in the present invention, a preferred method is melt-extrusion of the opioid agonist with matrix materials.

The active agent dispersed in a controlled-release matrix can be prepared by formulating, e.g., using dry or wet granulation or by blending, the active agent with a component other than the fusible component. Suitable non-fusible materials for inclusion in a controlled release matrix include, but are not limited to, any of the following:

(a) Hydrophilic or hydrophobic polymers, such as gums, cellulose ethers, protein-derived materials, nylon, acrylic resins, polylactic acid, polyvinylchloride, starches, polyvinylpyrrolidones, and cellulose acetate phthalate. Of these polymers, cellulose ethers, for example, substituted cellulose ethers such as alkylcelluloses (e.g., ethylcellulose), $C_1$-$C_6$ hydroxyalkylcelluloses (e.g., hydroxypropylcellulose and hydroxyethyl cellulose), and acrylic resins (e.g., methacrylates such as methacrylic acid copolymers) may be used. The controlled-release matrix can conveniently contain from about 1% to about 80% (by weight) of the hydrophobic and/or hydrophilic polymer.

(b) Digestible, long chain ($C_8$-$C_{50}$, in one embodiment $C_8$-$C_{40}$) substituted or unsubstituted hydrocarbons, such as fatty acids; hydrogenated vegetable oils; fatty alcohols, such as lauryl, myristyl, stearyl, cetyl or, in one embodiment cetostearyl alcohol; glyceryl esters of fatty acids, for example, glyceryl monostearate; mineral oils; and waxes, such as beeswax, glycowax, castor wax, and carnauba wax. Hydrocarbons having a melting point of from about 25° C. to about 90° C. are used in one embodiment. Of these long chain hydrocarbon materials, fatty (aliphatic) alcohols are useful in one embodiment. The controlled-release matrix can contain up to about 60% (by weight) of at least one digestible, long chain hydrocarbon.

(c) Polyalkylene glycols. The controlled-release matrix can contain up to about 60% (by weight) of at least one polyalkylene glycol.

A suitable controlled-release matrix for use in the oral dosage form of the invention comprises one or more cellulose ethers or acrylic resins, one or more $C_{12}$-$C_{36}$ aliphatic alcohols, in one embodiment $C_{12}$-$C_{22}$, aliphatic alcohols, and/or one or more hydrogenated vegetable oils. A particular suitable matrix comprises one or more alkylcelluloses, one or more $C_{12}$-$C_{36}$ aliphatic alcohols, in one embodiment $C_{12}$-$C_{22}$, aliphatic alcohols, and optionally one or more polyalkylene glycols. In another embodiment the matrix contains from about 0.5% to about 60% (by weight), and in another embodiment, from about 1% to about 50% of the cellulose ether.

The acrylic resin is, for example, a methacrylate such as methacrylic acid copolymer USNF Type A (EUDRAGIT L™), Type B (EUDRAGIT S™), Type C (EUDRAGIT L 100-55™), EUDRAGIT NE 30 D™, EUDRAGIT E™, EUDRAGIT RL™, or EUDRAGIT RS™ (commercially available from Röhm Pharma GmbH, Darmstadt, Germany). In one embodiment, the matrix contains from about 0.5% to about 95% by weight, and in another embodiment from about 10% to about 50% by weight of the acrylic resin.

In the absence of polyalkylene glycol, the matrix in one embodiment contains from about 1% to about 40%, in another embodiment from about 2% to about 36% (by weight) of the aliphatic alcohol. When polyalkylene glycol is present in the oral dosage form, then the combined weight of the aliphatic alcohol and the polyalkylene glycol in one embodiment constitutes from about 2% to about 40%, in another embodiment from about 2 to about 36% (by weight) of the matrix.

The polyalkylene glycol can be, for example, polypropylene glycol or, in one embodiment, polyethylene glycol. The number average molecular weight of the polyalkylene glycol is in one embodiment from about 200 to about 15,000 Daltons, and in another embodiment from about 400 to about 12,000 Daltons.

The controlled-release matrix containing the active agent can readily be prepared by dispersing the therapeutic agent in the components of the matrix using conventional pharmaceutical techniques including, but not limited to, melt-granulation, wet-granulation, dry-blending, dry-granulation, and co-precipitation.

The controlled-release formulations release, in one embodiment, slowly release, the therapeutic agent when ingested and exposed to gastric and/or intestinal fluids.

5.7 Co-Extrusion Process

The present invention also relates to methods for preparing a pharmaceutical composition or dosage form comprising a sequestered adverse agent by co-extruding, such as by melt co-extruding, a core comprising an adverse agent and a sheath which at least partially surrounds the core. In one embodiment, the invention relates to methods of making a plurality of sequestered adverse agent particles by a) co-extruding a core comprising an adverse agent, and a sheath which at least partially surrounds the core and preferably surrounds a majority of the core, to form extrudate strands; and b) cutting the extrudate strands to form a plurality of sequestered adverse agent particles. In one embodiment, the core comprises an adverse agent and a hydrophobic material and the sheath comprises a hydrophobic material.

In another embodiment, the invention relates to methods of making a dosage form comprising a) forming a plurality of first particles comprising an active agent; b) co-extruding a plurality of second particles comprising a sequestered adverse agent, wherein the second particles comprise a core comprising an adverse agent and a hydrophobic material, and a sheath comprising a hydrophobic material which at least partially surrounds the core, and preferably surrounds a majority of the core; and c) combining the first and second particles together.

Generally, methods of preparing active agent-containing compositions or particles by extrusion and/or co-extrusion are well known. See, for example, U.S. Pat. Nos. 5,958,452, 5,965,161 and 6,335,033, each of which is expressly incorporated herein in its entirety, which disclose known methods for extruding and forming pharmaceutical dosage forms, including dosage forms consisting of particles. Co-extrusion methods to form two layer compositions or particles for administering an active agent are also known. See, for example, U.S. Patent Application No. 2002/0119197 A1, which is expressly incorporated herein in its entirety. There is, however, no suggestion in the prior art of a co-extrusion method to form compositions or dosage forms comprising a sequestered ingredient, such as a sequestered adverse agent.

In accordance with the present invention, a co-extrusion process is used to make pharmaceutical compositions or dosage forms comprising a sequestered adverse agent which is released in a limited, if any, amount in vivo following intact administration as intended to a patient. In one embodiment, the composition or dosage form comprises a co-extruded, sequestered adverse agent cylindrical particle having a core containing the adverse agent and which is at least partially radially surrounded along its length by a sheath that preferably does not contain any adverse agent. In a further embodiment, the co-extruded particles containing a sequestered adverse agent, such as an opioid antagonist, are placed in a gelatin capsule with particles containing an active agent.

The present invention further relates to methods of preparing a particulate sequestered adverse agent useful in a dosage form, comprising charging an adverse agent core formulation comprising an adverse agent and a hydrophobic matrix material into a first extruder; charging a sheath formulation comprising a hydrophobic matrix material into a second extruder; heating the formulations in the first and second extruders; co-extruding the formulations to form a strand comprising an adverse agent core radially surrounded by a sheath; and rendering the strand into particles.

An example of an apparatus useful for the co-extrusion process of the present invention includes two powder-feeder hoppers, one for loading the adverse agent core components and one for loading the sheath components. The adverse agent core components include the adverse agent and the hydrophobic matrix material, and optionally additional materials including, but not limited to, additional retardants, binders, plasticizers and excipients, as described above. The sheath components include a hydrophobic matrix material and additional materials including, but not limited to, additional retardants, binders, plasticizers and excipients as described above. The contents of each hopper are charged to an extruder. The outlet of each extruder is attached to the same coaxial die having multiple co-axial outlet orifices, thereby forming strands of extrudate with the adverse agent in the core of the strand and the sheath radially surrounding the core so as to sequester the adverse agent.

Each extruder can, for example, be equipped with single or twin screws and heated barrels. Each screw extruder can, independently, be of the (i) counter-rotating (i.e., driven in opposite directions of rotation) non-intermeshing; (ii) co-rotating (i.e., driven in the same direction of rotation) non-intermeshing; (iii) counter-rotating intermeshing; or (iv) co-rotating intermeshing type. Each extruder can, independently, have a sole discharge port located at the end of its housing or a radial discharge port. Each screw extruder can, independently, have drive means at each end of the screw or a drive means present at only one end. Each screw extruder can, independently, have a length to diameter, or L/D, ratio of from 5-70, preferably from 20-60. Those in the art are familiar with such apparatuses, e.g., a Leistritz twin screw extruder having a vacuum attachment, a Leistritz Micro 18/GL 40D twin screw extruder, or a Warner & Pfleiderer model ZSK-30 twin screw extruder.

The temperature of each individually adjustable barrel zone of each extruder is set to the required temperature for a given formulation, and the extruder is allowed to thermally equilibrate, typically for about 30 minutes. The inside pressure of the twin screw extruder can be maintained from about 600 to about 980 mbar negative.

After a steady state temperature is attained, the contents of each powder-feeder hopper are fed into the separate pre-heated extruder, thereby forming in each extruder an intimately mixed molten mass typically from about 30° C. to about 200° C. in temperature, preferably from about 50° C. to about 150° C., through heating and mixing, as it is driven through a series of zones by intermeshing screws and kneading elements. Optionally, a vent port can be present in the extruder. If it is desired to add a liquid component, independently of any powdered formulation, to a molten mass, the liquid can be injected into the extruder by any known means, for example, by an injection port supplied by a positive displacement pump, such as a gear pump.

The molten masses exiting each extruder are combined in a coaxial die, which is optionally downstream of a combining block and/or a main gate adaptor, then passed through the exit orifice of the die, thereby forming a single or multiple extruded strand(s) comprising an adverse agent core and a sheath sequestering the core. Generally, the rotation speed, in rpm, of each extruder is adjusted such that their combined output, at the die orifice, is from about 1 to about 20 kg/hr or greater, preferably from about 6 to about 8 kg/hr. The rotation speed of each extruder is one of the parameters that can be adjusted so that the output of each extruder yields the desired ratio of the core to the sheath.

The dimensions and/or cross-sectional profile of the die exit orifice can be adjusted to vary the thickness and shape of the resulting strand. For example, the orifice is not limited to a circular cross-sectional profile, but can be elliptical, square, rectangular, hexagonal, triangular, 5-pointed star-shaped, etc. Typically, an orifice having a circular cross-section can be adjusted to provide a strand having a diameter from about 0.1 mm to about 5.0 mm. The shape of the strand is determined by, among other factors, the shape of the die exit orifice opening and the method of rendering the strand into particles.

The strand produced from the co-extrusion process is thereafter conveyed away from the orifice and solidified by methods known to those in the art, for example, using a fan-cooled tunnel or a continuous movable belt upon which the strand(s) congeal and harden upon cooling. The strand is directed to a suitable device to render the extruded strand into particles by methods known to those in the art, for example, using laser cutting, a hot wire-cutter or a guillotine. Rendering the strand into particles can occur before, during or following congealing.

In one embodiment, the hardened strand which results from the co-extrusion process is cut by a pelletizer, which can utilize rollers, a fixed knife, a rotating cutter and the like. The roller speed and cutter speed are set so as to produce particles of the desired size and release characteristics. Suitable instruments and systems are available from distributors such as Rand Castle Inc. of New Jersey. Other suitable apparatus will be apparent to those of ordinary skill in the art.

In one embodiment, the co-extruded strand is cut to form a number of cylinders as shown in FIG. 1, where the adverse agent-containing core is exposed at both ends of the cylinder. In any case, the compositions of the adverse agent-containing core and the sheath should be formulated accordingly to limit the rate of in vivo release of the sequestered adverse agent.

In addition, it is to be understood that the particles can be any geometrical shape within this size range, such as a bead, a seed, a pellet, etc., depending upon the die exit orifice. In one embodiment, the particulates formed will be spheroids with a diameter of from about 0.1 mm to about 3.0 mm. In another embodiment, the particulates formed will be cylindrical with a length of from about 0.1 to about 3.0 mm and a diameter of from about 0.1 to about 3.0 mm.

It will be apparent to one of ordinary skill in the art of pharmaceutical extrusion that the dimensions of the core and the sheath can be varied. For example, by changing the die orifice, the diameter of the core and the thickness of the sheath can be varied. Typically, the diameter of the core is from about 0.05 mm to about 2.95 mm, preferably about 0.3 mm to about 2.0 mm. The thickness of the sheath is determined by the stability of the hydrophobic matrix material and the thickness of the core. Typically, the thickness of the sheath is from about 0.05 mm to about 2.95 mm, preferably about 0.3 mm to about 2.0 mm. The diameter of the core and the thickness of the sheath are typically adjusted to provide a particulate with a cross-sectional diameter of about 3.0 mm or less. By routine experimentation, one skilled in the art of extrusion can modify the parameters in order to prepare the adverse agent-containing particles with suitable dimensions.

Following cutting, the co-extruded particles are collected and can be used in any manner for which such solid pharmaceutical composition is used. Optionally, following cutting, the particles are passed through a separator using #16 TBC (approximately 0.054") and #26 TBC (approximately 0.031") opening screens and collected. In a preferred embodiment, co-extruded particles containing an adverse agent and particles containing an active agent are placed together in hard gelatin capsules for oral dosage to patients.

5.8 Methods for Administration

The present invention is also directed to methods for treating a condition in a patient comprising administering a dosage form of the present invention to a patient in need of said treatment. The dosage form, can be, for example, an oral dosage form, such as a tablet or capsule, or a rectal or vaginal dosage form, such as a suppository. In one embodiment, the condition is pain and the dosage form comprises an opioid and a sequestered opioid antagonist. In certain embodiments, the dosage form is administered to a patient twice a day, and in other embodiments, once a day.

5.8.1 Amount Per Dosage Unit

In the dosage form of the present invention, the amount of the active agent per dosage unit is that which is an effective amount for its particular indication and is independent of the amount of the adverse-effect agent. For example, if the therapeutic agent is an opioid agonist, the amount of the opioid agonist in the dosage form of the present invention is generally from about 1 mg to about 800 mg, in one embodiment from about 5 mg to about 160 mg. One of ordinary skill in the art can readily determine, without undue experimentation, the amount of therapeutic agent needed for a particular indication.

The amount of the adverse agent in the dosage form of the present invention is such that the adverse agent can give the intended adverse effect if, when tampered with, a substantial amount of the adverse agent is released immediately from the dosage form and absorbed into an animal's blood. When, upon tampering with the dosage form, the adverse agent is intended to reduce or eliminate one or more of the pharmacological effects of the active agent, such as euphoria, the amount of the adverse agent in the dosage form is at least sufficient to reduce or eliminate those effects of the active agent when substantial amounts of both agents are released from the dosage form and absorbed into an animal's blood after tampering has occurred.

When the adverse effect agent is an opioid antagonist, such as naltrexone or nalmefene, the amount of the opioid antagonist present in a dosage form of the present invention can be from about 0.2 mg to about 50 mg, or from about 0.5 mg to about 5 mg. The opioid antagonists cyclazocine and naltrexone, when administered orally, retain much of their efficacy with a long duration of action, approaching 24 hours. Amounts of less than about 10 mg of these opioid antagonists are typically used in oral formulations of the invention.

When, upon tampering, the adverse effect agent is intended to cause an undesired physiological reaction, such as emesis, the amount of the adverse-effect agent in the dosage form is at least sufficient to cause such effect upon release after tampering has occurred.

In certain embodiments of the present invention, the ratio of the therapeutic agent to the adverse-effect agent in the dosage form can be from about 1:1 to about 50:1 by weight, in one embodiment from about 1:1 to about 20:1 by weight. In certain other embodiments, the ratio may can be about 1:1 to about 10:1 by weight.

In non-limiting embodiments in which the opioid agonist is hydrocodone, the sustained-release dosage forms can include analgesic doses from about 5 mg to about 80 mg of hydrocodone per dosage unit. In non-limiting embodiments where the opioid agonist is hydromorphone, it can be included in an amount from about 2 mg to about 64 mg hydromorphone hydrochloride per dosage unit. In non-limiting embodiments in which the opioid agonist is morphine, it can be present in the dosage form from about 2.5 mg to about 800 mg morphine per dosage unit. In non-limiting embodiments in which the opioid agonist is oxycodone, the dosage forms can include from about 2.5 mg to about 800 mg oxycodone, and in another embodiment from about 20 mg to about 30 mg oxycodone per dosage unit. Controlled-release oxycodone formulations are known in the art. In a non-limiting embodiment, the opioid agonist can be tramadol in an amount from about 25 mg to 800 mg tramadol per dosage unit. The dosage form can contain more than one opioid agonist, and the doses of each can be adjusted accordingly.

The term "unit dose" is defined for purposes of the present invention as the total amount of dosage form needed to administer a single desired dose of active agent (e.g., opioid agonist) to a patient.

5.8.2 Methods for Rectal Administration

As noted above, the present invention is also directed to administration of a dosage form comprising co-extruded, sequestered adverse agent particles and active agent particles to a patient in need thereof in the form of a suppository for absorption through the rectum. When administered as a suppository, the composition preferably comprises a base material. Any base material can be used provided it does not dissolve the particulates. For example, cocoa butter is a traditional suppository base material, which can be modified by addition of waxes to raise its melting point slightly. Water-miscible suppository base materials comprising, particularly, polyethylene glycols of various molecular weights can be included. When administered as a suppository, the combined concentration of the first and second plurality of particles in the suppository formulation is, typically, from about 5.0% to about 80% by weight of the composition.

5.8.3 Kits

The present invention is also directed to a kit comprising at least one dosage form of the invention. In one embodiment, the dosage form is present in a container, e.g., a bottle or box. In another embodiment, the kit further comprises a set of instructions directing the use of the dosage form to treat a patient, e.g., for pain. In one embodiment, the instructions may be a printed label affixed to or printed on the container. In another embodiment, the instructions may comprise a printed sheet inserted into the container or into the packaging which contains the container. The instructions may also state that the dosage form and/or its usage are designed to reduce abuse, misuse or diversion of the dosage form.

6. EXAMPLES

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the present invention.

6.1 Example 1: Preparation of Unsheathed Sequestered Opioid Antagonist Particles by Melt Extrusion Example 1 describes the preparation of unsheathed, sequestered opioid antagonist particles. The formulation of the feed to the extruder used to prepare the opioid antagonist-containing particles is provided in Table 1 below.

TABLE 1

Formulation Used to Prepare Unsheathed Sequestered Naltrexone Hydrochloride Particles by Melt Extrusion.

| Ingredient | Amount/Unit (mg) | Content in Feed (wt. %) |
|---|---|---|
| Naltrexone hydrochloride | 2 | 1.7 |
| EUDRAGIT RS PO | 88 | 72.7 |
| Stearyl alcohol | 15 | 12.4 |
| Stearic acid | 15 | 12.4 |
| BHT | 1 | 0.8 |
| Total | 121 | 100 |

Unsheathed, sequestered opioid antagonist (naltrexone HCl) particles were prepared by charging the ingredients of Table 1 to the powder-feeder hopper of a Leistritz twin screw extruder having a vacuum attachment. The extruder was equipped with twin-screws and a multi-zone heated barrel. The initial zones were maintained at a target temperature of 50±2° C., intermediate zones were maintained at a target temperature of 105±3° C., and final zones were maintained at a target temperature of 70±2° C. The inside pressure of the twin screw extruder was maintained from about 600 to about 980 mbar negative. The inlet end of the extruder barrel was adjacent to the powder-feeder hopper, and the outlet end was attached to a die with circular cross-section orifices about 1 mm in diameter. The extruder was allowed to thermally equilibrate for 30 minutes.

The rotation speed of the extruder was set to a level to produce the desired output, and the formulation was heated with mixing until a molten mass formed. The resultant viscous mass was transported through the pre-heated barrel to the die, and the viscous formulation was extruded through circular cross-section die orifices about 1 mm in diameter as spaghetti-like strands. The extrudate was transported on a continuous movable belt to a pelletizer as it congealed and hardened. The resultant hardened strands are pelletized with a Rand Castle Inc. roller knife into cylindrical particles of about 1.0 mm in diameter and about 1.0 mm in length.

After the pellets were manufactured, 121 mg of pellets were encapsulated in hard gelatin capsules, rendering capsules containing 2 mg of Naltrexone HCl. These capsules were then tested using the following dissolution methodology:

The dissolution rate of the capsules was measured by the USP Basket Method. The apparatus consisted of a USP Type I basket (100 rpm). The capsules were contacted with 700 mL simulated gastric fluid (SGF), (pH 1.2 without enzyme) at 37° C. for one hour. Thereafter, the capsules were contacted with 900 mL simulated intestinal fluid (SIF) (pH 7.5 without enzyme) for the duration of the test. The rate of dissolution was determined by assaying each of the fluids using HPLC.

Capsules prepared by the above process exhibited dissolution rates set forth in Table 2.

TABLE 2

Rate of Dissolution of Unsheathed Sequestered Core Particles Containing Naltrexone Hydrochloride in Hard Gelatin Capsules.

| | Time (hr) | | | | | | |
|---|---|---|---|---|---|---|---|
| | 1 | 2 | 4 | 8 | 12 | 24 | 36 |
| Mean % dissolved | 1.3 | 2.6 | 2.9 | 3.6 | 4.0 | 5.2 | 6.2 |

6.2 Example 2: Preparation of Sheathed Sequestered Opioid Antagonist Particles by Melt Co-Extrusion Example 2 describes a prophetic example of a process which should be suitable for the preparation of a sheathed, sequestered opioid antagonist particle by melt co-extrusion, where the core contains the sequestered opioid antagonist naltrexone hydrochloride and a majority of the core is surrounded by a sheath which does not contain any naltrexone. More particularly, the core is cylindrical, and the sheath surrounds the length of the core in the radial direction while the ends of the core are exposed in the axial direction. The formulations of the feed to the core extruder and the feed to the sheath extruder that may be used in this prophetic example are provided in Table 3.

TABLE 3

Formulation to Prepare Sheathed Sequestered Naltrexone Hydrochloride Particles by Melt Co-extrusion.

| Ingredient | Amount (mg) | Content (wt. %) |
|---|---|---|
| Core Formulation: | 61 | 50.8 |
| Naltrexone HCl | 2 | 1.7 |
| EUDRAGIT RS PO | 44 | 36.7 |
| Stearyl alcohol | 7 | 5.8 |
| Stearic acid | 7 | 5.8 |
| BHT | 1 | 0.8 |
| Sheath Formulation: | 59 | 49.2 |
| EUDRAGIT RS PO | 44 | 36.7 |
| Stearyl alcohol | 15 | 12.5 |
| Total | 120 | 100 |

The core of the sheathed, sequestered opioid antagonist (naltrexone HCl) particles can be prepared by 1) charging the core formulation ingredients of Table 3 into the powder-feeder hopper of a Leistritz twin screw core extruder having a vacuum attachment; and 2) charging the sheath formulation into the powder-feeder hopper of a Leistritz twin screw sheath extruder having a vacuum attachment. Each extruder can be equipped with twin-screws and a multi-zone heated barrel. In each extruder, the initial zones can be maintained at a target temperature of 50±2° C.; intermediate zones can be maintained at a target temperature of 105±3° C.; and final zones can be maintained at a target temperature of 70±2° C. Each extruder can be allowed to thermally equilibrate for 30 minutes. The inside pressure of each twin screw extruder can be maintained from about 600 to about 980 mbar negative. The inlet of each extruder barrel can be attached to the outlet end of the respective powder-feeder hopper. The outlet of the core extruder barrel can be connected to the inlet of the core orifice of a co-extrusion die and the outlet of the sheath extruder barrel can be attached to the inlet of the sheath orifice of the co-extrusion die. The extrudate strand which exits the co-extrusion die comprises a cylindrical core containing sequestered naltrexone HCl which is surrounded in the radial direction by an annular-shaped sheath.

The rotation speed of each extruder can be set to a level to produce the desired combined output, at the die orifice, such as 7 kg/hr. The formulations can be heated with mixing until respective molten masses form. Each resultant viscous mass can then be transported through the respective extruder barrel to the respective co-extrusion die inlets. The extrudate can then be transported on a continuous movable belt to a pelletizer as it congeals and hardens. The resultant hardened strands can be pelletized with a Rand Castle roller knife into cylindrical particles of about 0.5 to 1.5 mm in diameter and about 1.0 mm in length; for example about 0.8 to 1.4 mm in length and about 0.8 to 1.2 mm diameter. In these particles, the average diameter of the core is about 0.25 to 0.5 mm and the average thickness of the sheath is about 0.25 to 0.5 mm.

After their manufacture, 120 mg of the co-extruded particles can be encapsulated in hard gelatin capsules described in Example 1 to provide capsules containing 2 mg of naltrexone hydrochloride.

The rate of dissolution of the naltrexone hydrochloride released should then be measured as described in Example 1. The amount of naltrexone hydrochloride released from the co-extruded, sheathed, sequestered opioid antagonist particles of Example 2 is expected to be less than the amount released from the particles of Example 1.

All patents, applications, publications, test methods, literature, and other materials cited above are hereby incorporated herein by reference.

What is claimed is:

1. A method of making a plurality of adverse agent particles comprising:
    co-extruding a core composition and a sheath composition to form an extrudate stand; wherein the sheath composition radially surrounds, at a constant thickness along substantially its entire length, at least a majority of the core composition, the core composition comprises an adverse agent and a hydrophobic material, and the sheath composition comprises a hydrophobic material; wherein the constant thickness of the sheath composition ranges from about 0.05 mm to about 2.95 mm; and
    cutting the extrudate strand at predetermined lengths to form a plurality of adverse agent particles,
    wherein the adverse agent comprises an opioid antagonist.

2. The method of claim 1, wherein the particles have a size of about 0.1 mm to about 3.0 mm in all dimensions.

3. The method of claim 1, wherein the adverse agent is sequestered.

4. A method of making a dosage form comprising:
    (a) forming a plurality of first particles comprising an active agent comprising an opioid agonist;
    (b) forming a plurality of second particles comprising an adverse agent by co-extruding a core composition and a sheath composition to form an extrudate strand; wherein the sheath composition radially surrounds, at a constant thickness along substantially its entire length, a portion of the core composition, the core composition comprises the adverse agent and a hydrophobic material, and the sheath composition comprises a hydrophobic material; and cutting the extrudate strand at predetermined lengths to form a plurality of second particles; wherein the adverse agent comprises an opioid antagonist; and wherein the constant thickness of the sheath composition ranges from about 0.05 mm to about 2.95 mm; and
    (c) adding the first particles and the second particles together in a form suitable for administration to a patient.

5. The method of claim 4, wherein the first particles and the second particles are substantially identical in appearance to each other.

6. The method of claim 4, wherein the dosage form is an oral dosage form, and the first particles and the second particles each have a size of from about 0.1 mm to about 30 mm in all dimensions.

7. The method of claim 4, wherein the first particles and the second particles are placed into a capsule for administration to a patient.

8. The method of claim 4, wherein the adverse agent is sequestered.

* * * * *